United States Patent [19]

Khan et al.

[11] Patent Number: 4,925,668

[45] Date of Patent: May 15, 1990

[54] ANTI-INFECTIVE AND LUBRICIOUS MEDICAL ARTICLES AND METHOD FOR THEIR PREPARATION

[75] Inventors: Mohammad A. Khan, Sandy, Utah; Donald D. Solomon, Spring Valley; Matthew P. Byron, Centerville, both of Ohio

[73] Assignee: Becton, Dickinson and Company, Franklin Lakes, N.J.

[21] Appl. No.: 298,393

[22] Filed: Jan. 18, 1989

[51] Int. Cl.$^5$ .............................................. A61L 33/00
[52] U.S. Cl. ................................... 424/422; 424/423; 427/2; 523/112; 523/113; 523/122; 604/265; 604/317
[58] Field of Search ............... 523/112, 113, 122; 424/405, 404, 422, 423, 443; 427/2; 604/265, 317

[56] References Cited

U.S. PATENT DOCUMENTS

| | | | |
|---|---|---|---|
| 4,117,035 | 9/1978 | Hillier et al. | 523/112 X |
| 4,186,745 | 2/1980 | Lewis et al. | 128/349 R |
| 4,460,369 | 7/1984 | Seymour | 424/448 |
| 4,604,412 | 8/1986 | Joh et al. | 523/112 |
| 4,675,347 | 6/1987 | Mochizuki et al. | 523/122 |
| 4,806,621 | 2/1989 | Kohn et al. | 523/113 X |

*Primary Examiner*—Thurman K. Page
*Attorney, Agent, or Firm*—Richard E. Brown

[57] ABSTRACT

A substantially hydrophilic polymeric medical article has a coating of chlorhexidine and a silicone on its surface and may have chlorhexidine bulk distributed throughout the polymer. The invention includes a method for preparing the article which includes dipping the article into a solution of chlorhexidine and silicone in a solvent. The method may also include preparing a melt of a substantially hydrophilic polymer having bulk distributed chlorhexidine by twin screw compounding a mixture of polymer and chlorhexidine and extruding the melt into the shape of the desired article prior to applying the coating.

19 Claims, 1 Drawing Sheet

U.S. Patent   May 15, 1990   4,925,668
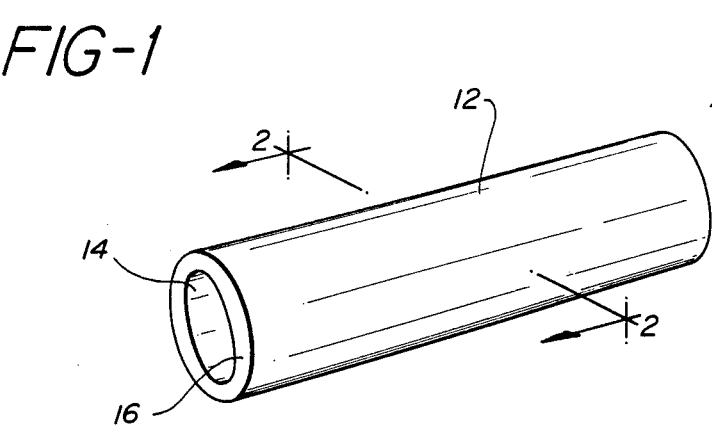
FIG-1
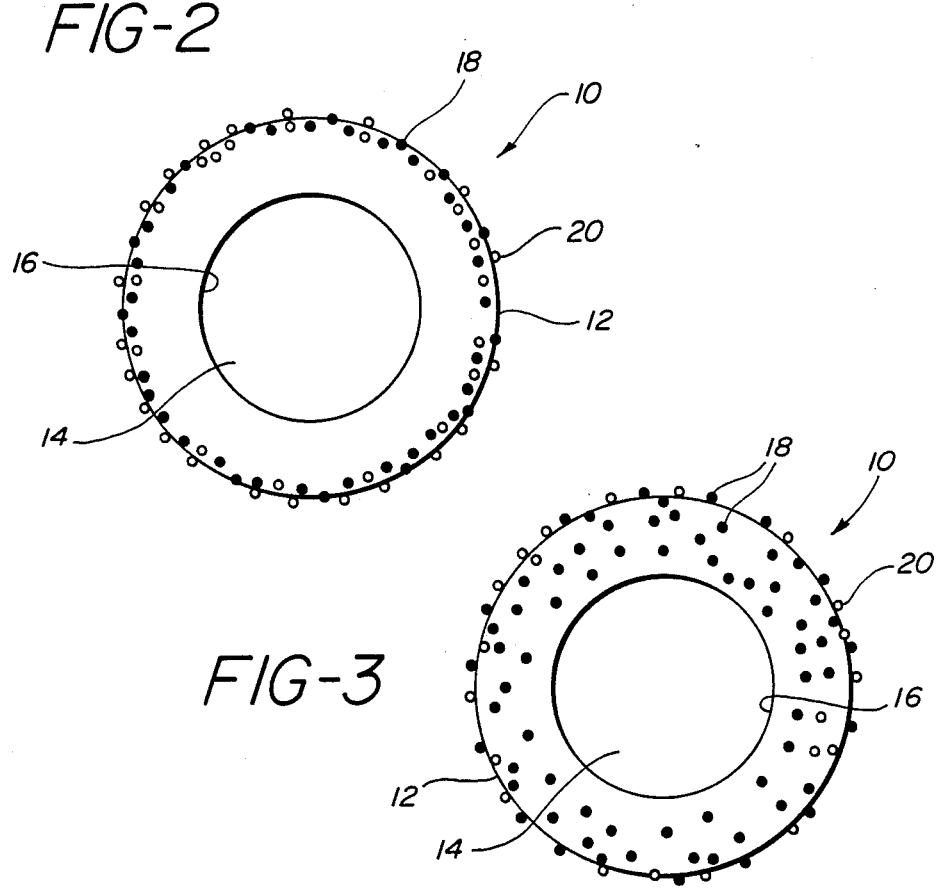
FIG-2
FIG-3

ANTI-INFECTIVE AND LUBRICIOUS MEDICAL ARTICLES AND METHOD FOR THEIR PREPARATION

BACKGROUND OF THE INVENTION

1. Field of the Invention

This invention relates to medical articles, and, more particularly, relates to lubricious articles which inhibit or reduce bacterial growth in a living body during their use and to their preparation.

2. Background of the Invention

Polymeric materials such as polypropylene, polytetrafluoroethylene and polyurethane are frequently used to fabricate medical articles. These materials are for the most part inherently nonlubricious, yet are often used in invasive techniques such as catheterization in which a lubricious surface would contribute to patient comfort. Another problem encountered during use of medical articles which come into contact with a body tissue or fluid is infection, and a desirable feature of such articles is some means to control this complication. Accordingly, a variety of approaches to introduce these two features to plastic articles has been disclosed.

Spielvogel et al., in U.S. Pat. No. 4,720,521, teaches adherence of a lubricating composition to a surface. The composition includes a polysiloxane lubricant entrapped in a mixture of a plurality of reactive silicone components which, on curing, adhere to the surface and provide lubricity.

Many attempts to solve the problem of infection have been directed toward adherence of an antibacterial agent to the plastic article. Gould et al., in U.S. Pat. No. 3,695,921, discloses a catheter coated with a layer of hydrophilic polymer having an antibiotic absorbed therein.

EP published application No. 229,862 teaches thermoplastic polyurethane medical devices having an antimicrobial agent on its surface.

Fox et al., in U.S. Pat. No. 4,581,028, teaches infection resistant plastic medical articles, such as vascular grafts, having incorporated antimicrobial agents, such as silver sulfadiazine and pipericillin. The articles are prepared by dipping procedures.

Mustacich et al., in U.S. Pat. No. 4,479,795, discloses medical devices of permeable polymers including a releasably incorporated coating of a carboxylate antimicrobial agent which diffuses to the surface of the device to form an antimicrobial barrier.

In Japanese patent application No. SHO 60-36064 a polyurethane or silicone catheter is dipped into an aqueous solution of chlorhexidine to absorb the chlorhexidine into the polymer. The chlorhexidine is then converted to a water insoluble form by dipping into a solution of an acid. Japanese Pat. No. 59,228,856 discloses an elastomeric catheter having a water insoluble biguanide or salt thereof incorporated as a thin coating membrane in the surface of the catheter.

PCT published application No. WO 86/02561 teaches a medical device of a hydropho-bic thermoplastic polymer having up to 1% chlorhexidine base coated thereon or incorporated therein.

UK patent application No. 2,084,466A discloses a polypropylene article rendered biocidal with chlorhexidine base, and suggests that the article may be prepared from other plastics.

Solomon et al., in U.S. Pat. No. 4,713,402, discloses a method for attachment of a quaternary salt to the surface of a polymeric article and affixation of an antibiotic or antithrombogenic agent to the salt.

Although all of the above disclosures have addressed the separate problems of infection control and lubricity during use of medical articles, completely satisfactory solutions even to the individual problems have not yet been disclosed. The present invention is directed toward providing a common solution to both problems.

SUMMARY OF THE INVENTION

A method for preparing a lubricious, anti-infective medical article includes applying to a surface of the article a coating of an anti-infective agent and a silicone lubricant. Preferably, the coating is applied by dipping the surface into a solvent solution of the anti infective agent and lubricant and evaporating the solvent. The term anti infective agent is herein intended to mean any agent which inhibits bacterial growth, and thus includes antibiotics, antibacterial agents, antiviral agents and antimicrobial agents.

A preferred method of the invention includes preparing a homogeneous melt of a substantially hydrophilic polymer and the anti infective agent and extruding the melt through a die to form a medical article having the anti infective agent distributed substantially evenly throughout the bulk of the polymer (hereinafter referred to as bulk distributed) prior to applying the surface coating.

The melt is preferably prepared by blending polymer pellets and chlorhexidine until an even coating of chlorhexidine on the polymer is obtained, followed by heating to give a homogeneous melt. Most preferably, polymer pellets and chlorhexidine powder are simultaneously blended and melted by twin screw compounding followed by heating to a temperature sufficient to form the homogeneous melt.

Preferred polymers are siloxaneurethane copolymers, or, most preferably, polyurethanes and polyurethaneureas. The chlorhexidine may be either in the form of the free base or, preferably in the form of a salt such as the hydrochloride, acetate and gluconate.

Another aspect of the invention is a medical article having a layer of chlorhexidine, preferably a chlorhexidine salt and silicone oil coated onto the surface of the article. The preferred article of the invention additionally has chlorhexidine base or a salt thereof bulk distributed throughout the article. The most preferred article of the invention is a tubing, most preferably a catheter treated in accordance with the method of the invention.

Thus, the invention provides a method to prepare a lubricious anti-infective article from a high melting hydrophilic polymer having mechanical properties providing advantages not afforded by polymers of lower melting point. The preferred article has a surface layer of silicone and chlorhexidine which is rapidly released and bulk distributed chlorhexidine which is released slowly providing a long lasting anti infective effect.

BRIEF DESCRIPTION OF THE DRAWINGS

FIG. 1 is a perspective view of a typical polymeric tubing of the invention;

FIG. 2 is a cross sectional view of the tubing of FIG. 1 taken along the line 2—2 thereof showing chlorhexidine and silicone on the surface thereof; and FIG. 3 is a cross sectional view of the tubing of FIG. 1 taken along the line 2—2 thereof showing chlorhexidine bulk distributed throughout the tubing and chlorhexidine and silicone on the surface thereof.

DETAILED DESCRIPTION

While this invention is satisfied by embodiments in many different forms, there will herein be described in detail preferred embodiments of the invention, with the understanding that the present disclosure is to be considered as exemplary of the principles of the invention and is not intended to limit the invention to the embodiments illustrated and described. The scope of the invention will be measured by the appended claims and their equivalents.

In accordance with the present invention, a significant reduction of infection and patient discomfort associated with the use of medical articles is achieved by combining an anti infective agent and a lubricant with the article. If the anti infective agent can form a salt, the article of the invention is contemplated to include the salt form of the agent as well as the parent (nonsalt) form.

A variety of anti infective agents as known in the art may be used, including antibiotics, such as penicillin, and antibacterial agents such as silver sulfadiazine, hexitidine and bronopal. In some cases, it may be desirable to provide dual anti infective action with two or more agents. The invention will be described in terms of the preferred chlorhexidine, a biguanide of known safety and high activity against a wide variety of organisms, including gram negative and gram positive bacteria and yeasts, with the understanding that the invention contemplates any anti infective agent which may be combined with a lubricant and coated onto the surface of the polymer by the method of the invention.

The medical article of the invention may be any medical article compatible with chlorhexidine which, absent the chlorhexidine, may lead to infection when in contact with a body tissue or fluid. Exemplary of, but not limited to, such articles are vascular access (arterial and venous) catheters, including sensing and monitoring catheters, introducers, vascular grafts, urinary catheters and associated articles, such as drainage bags and connectors, and all abdominal cavity drainage tubing, bags and connectors. Preferred articles are polymeric. The most preferred article of the invention is a polymeric vascular access catheter.

Selection of a polymer to be used for catheter fabrication requires a balancing of several properties. First, the catheter must be stiff enough to be inserted into, for example, a blood stream, without kinking. However, once in contact with the blood, it should preferably soften and become sufficiently flexible to bend and be advanced through the tortuous path of the vessel.

Polymers which exhibit suitable mechanical and hydrophilic behavior for fabrication of the catheter of the invention are, for example, substantially hydrophilic, polyurethanes, polyurethaneureas, and siloxane urethane block copolymers. Preferred polymers are polyurethanes or polyurethaneureas having a resin hardness of about 50 A to 75 D when measured under standard room conditions of 23° C. and 50% relative humidity, and a water absorption capacity of about 1.0 to 6.0%, preferably about 1.5 to 3.0% (all percentages given herein are by weight unless otherwise stated). Exemplary of suitable polymers and their hardness and water absorption percentages are polyurethane 80 A (1.85%), polyurethane 55 D (1.66%), polyurethaneurea 70 A (1.94%), silicone urethane copolymer 70 A (1.87%) and silicone urethane copolymer 65 D (1.88%). Polyolefins in contrast are hydrophobic, absorbing about 0.04 to 0.4% water, and are unsuitable for the present invention because, as shown in Example IV, they remain rigid inflexible and unable to advance through winding blood vessels without kinking rubbing against the vessel wall causing irritation, patient discomfort and possibly phlebitis.

Various embodiments of the article having a layer of chlorhexidine and silicone coated onto its surface are contemplated to fall within the scope of the invention. The article may additionally have chlorhexidine bulk distributed in the article. Different concentrations of bulk distributed or surface coated chlorhexidine, or two or more different anti infective agents may be included. The preferred article of the invention has a layer of chlorhexidine and silicone coated onto the surface of the article and bulk distributed chlorhexidine therein.

Articles of the invention having bulk distributed chlorhexidine may be prepared by extruding a melt of the polymer and chlorhexidine through a die. The chlorhexidine may be melted or may be a solid uniformly distributed in the polymer melt. The melt to be extruded may contain about 0.05% to 10%, preferably about 1 to 5% by weight of chlorhexidine, and may be prepared in any suitable way. For example, the polymer and chlorhexidine may be melted, and the melts combined and mixed thoroughly. While blending of separate melts may be performed, this method is less preferred because the high viscosities of the melts makes uniform blending difficult resulting in an article having a rough surface.

The preferred method for preparing the melt for extrusion is to blend the polymer and chlorhexidine in particulate form prior to melting. In general, particulate blending may be carried out by any suitable mixing technique, such as stirring the polymer pellets and chlorhexidine powder together, or, preferably, by tumbling. This method is straightforward and is the method of choice for preparation of melts of polyurethanes and chlorhexidine base. It has been found, however, that particulate chlorhexidine salts and polyurethane pellets do not form uniform blends by these conventional procedures when the concentration of the salt is greater than about 1% by weight. If the salt and pellets are not uniformly blended prior to melting, the melt and therefore the extruded article will contain nonhomogeneously distributed salt and, as a consequence, significant areas of rough surface having little or no salt.

In order to prepare uniform blends of higher salt concentration, the polymer pellets may first be surface wetted by thorough mixing of the pellets with about 0.1 to 2% by weight of a polyol. Any suitable polyether or polyester polyol may be used, as, for example, polytetramethylene oxide (PTMO) having a molecular weight of about 500 to 3,000. These products are well known and are commercially available.

A preferred method for blending chlorhexidine salts uniformly with polymer pellets is to melt and repelletize the ingredients with a twin screw compounder. The polymer pellets, chlorhexidine salt and other ingredients such as fillers and pigments, may be fed to the compounder at a suitable rate. In the compounder, the ingredients are melted and blended and then extruded into strands. The strands may be pelletized and dried prior to further processing. A corotating intermeshing twin screw extruder may be used, such as Model ZDSK-28 from Werner and Pfleiderer Corp., Ramsey, N.J.

The homogeneous pellets of polymer and chlorhexidine prepared as described above may be remelted and molded or extruded into the desired shape of the medical article. For the preferred catheter of the invention, the melt may be extruded into tubing using conventional equipment, such as, for example, a Killion extruder with a one inch diameter barrel and a 24:1 (1/d) screw.

The temperature processing range for uniform blends of particulate chlorhexidine and polymer depend on the polymer being extruded. In general, mëlting and extrusion may be performed over a temperature range of about 160° to 250° C., preferably about 200°-235° C.

The article of the invention, with or without bulk distributed chlorhexidine, may be dipped into a solvent solution of chlorhexidine and a silicone lubricant whereby a layer of chlorhexidine and lubricant is applied to the surface of the article. An effective coating of chlorhexidine may be obtained when the solvent solution contains from about 0.02 to 5%, perferably about 0.1 to 3.0% of chlorhexidine and about 0.1 to 8, preferably 1 to 4% of silicone. Accordingly, the choice of solvent depends on the solubility of the chlorhexidine and silicone and on the temperature contemplated for the dipping solution. Suitable solvents to serve as the dipping medium are alcohols and aqueous alcohols such as ethanol and isopropanol, hydrocarbons such as hexane and Freon$^R$ TF and preferably ethanol-dichlorodifluoromethane. It is, of course, understood that technigues other than dipping, such as brushing or spraying, may be used, and that the solvent may be removed from the article by any conventional procedure, such as evaporation, with or without heat and reduced pressure.

The lubricant/antimicrobial may be applied by a quick dip of the article into the solution at ambient temperature. The dipping time and temperature may be modified to alter the coating characteristics as desired. It is, of course, evident that the coating may be formed on either or both the outside and lumen walls of the catheter merely by contacting the desired walls with the dipping solution. Thus, dipping solution may be drawn into the lumen for contact with the lumen wall only, or preferably the lumen may be filled with a solid rod so that the dipping solution contacts only the outside wall.

A suitable lubricant is a silicone oil or a mixture thereof having a molecular weight of about 20,000 to 60,000, preferably about 35,000 to 45,000. Preferred lubricants are polydialkylsiloxanes of general structure I:

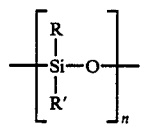

wherein each of R and R may be independently a lower alkyl of 1 to 20 carbon atoms, preferably 1 to 8 carbon atoms, or may be joined into a silicon containing ring of 5 to 8 carbon atoms, and n may be an integer from 1 to 2000, preferably 1 to 800. The preferred lubricants of structure I have viscosities of from about 10 to 1,000,000, preferably about 100 to 20,000 centistokes.

The most preferred lubricant is DC-360$^R$ silicone oil of 12,500 centistokes (Dow Corning).

The preferred catheter of the invention includes a polymer having both bulk distributed chlorhexidine and a coating of chlorhexidine and silicone. This embodiment of the invention produces lubricity and a dual anti infective activity. The surface coating provides a readily available and rapid release of chlorhexidine. The bulk distributed chlorhexidine, due to the hydrophilic nature of the polymer, migrates slowly to the surface when the catheter is in contact with a body fluid and produces anti infective activity of long duration.

The lubricious anti infective catheter of the invention will now be described in more detail with the aid of the drawings. FIG. 1 shows polymeric catheter tubing 10 having an outside wall 12, a lumen 14 and a lumen wall 16. FIG. 2 shows tubing 10 having chlorhexidine molecules 18 and silicone molecules 20 coated onto the surface of outside wall 12. FIG. 3 shows the catheter of FIG. 2 which additionally has chlorhexidine molecules 18 bulk distributed throughout the polymer.

The following examples are provided to further illustrate typical catheter preparations of the invention and an in vitro procedure for determining their anti infective properties.

EXAMPLE I

Preparation of Polyurethane Tubing Having Bulk Distributed Chlorhexidine Diacetate and a Surface Coating of Chlorhexidine Diacetate and Silicone Oil Polyurethane pellets were blended with 5% chlorhexidine diacetate powder with the Werner and Pfleiderer, Model ZDSK-28 twin screw compounder and the well blended mixture was extruded into 16 guage tubing using a Killion one inch extruder at approximately 175°. The lumen was filled with a solid rod and dipped into a solution containing 0.2% chlorhexidine diacetate and 2.0% DC 360$^R$ silicone oil in ethanol-Freon$^R$ TF for about 10 seconds at ambient temperature. The rod was removed and the solvent removed by evaporation at ambient temperature.

EXAMPLE II

Preparation of Polyurethane Tubing Having a Surface Coating of Chlorhexidine Diacetate and Silicone Oil A 16 gauge polyurethane catheter tubing absent bulk distributed chlorhexidine was coated as described in Example I with a solution of 2.4% of DC 360$^R$ silicone oil in ethanol Freon TF containing 0.2, 0.25, 0.3 and 0.35% chlorhexidine diacetate. The following zones of inhibition were determined in accordance with the procedure of Example III.

ZONES OF INHIBITION (mm)

| | ZONES OF INHIBITION (mm) | | | |
|---|---|---|---|---|
| | Concentration of Chlorhexidine | | | |
| Organism | 0.2% | 0.25% | 0.3% | 0.35% |
| S. epidermidis | 7 | 7 | 7 | 7 |
| E. coli | 3.5 | 4.5 | 4.5 | 5.5 |
| S. aureus | 6.5 | 7.5 | 8 | 8 |
| C. albicans | 3.5 | 4 | 4 | 4.5 |
| P. aeruginosa | 0 | 0 | 1.5 | 1.5 |

EXAMPLE III

In vitro Test for Anti Infective Activity

In vitro antimicrobial activity of the anti-infective tubing of the invention was measured by a standard zone of inhibition test. A broth of the test organism, such as *S. aureus*, was started from standard disks (Bactrol) in trypticase soy broth (TSB) and allowed to grow overnight. A 0.2 ml aliquot of the overnight broth was transferred to a fresh solution of TSB and allowed to grow for 2 to 5 hours until the turbidity of the solution was equivalent to a 1% barium sulfate standard solution. A 0.2 ml aliquot of this broth was transferred to a Mueller Hinton (M-H) agar plate and spread evenly on the surface. Medical tubings of the invention were cut into suitable lengths of 1.5 cm and embedded into the surface of the agar. The plates were then cultured 16 hours (overnight). Plates were evaluated for the inhibition of bacterial growth visually by the unaided eye. Zones were measured in millimeters across the axis of the tubing, the measurement including the diameter of the medical article.

EXAMPLE IV

Comparison of the Flexibility of Polyolefins and Urethane Polymers

In accordance with the procedure of Zdrahala et al. (Polyurethanes in Biomedical Engineering, II, H. Planck et al., ed., Elsevier Science Publishers B.V. Amsterdam, 1987, p 1-18), pieces of 16 gauge polyurethane (65D) and polypropylene tubing were tested for the effect of absorbed water on tubing stiffness on the Instron Model 1122 Universal Testing Machine. Bending forces in grams were determined after 24 hours under ambient conditions of 23° C. and 50% relative humidity and after soaking in normal saline for 24 hours at 23° C. The following results were obtained:

|  | Bending Force, gr | |
|---|---|---|
|  | ambient | soak |
| polypropylene | 331 | 368 |
| polyurethane | 224 | 84 |

It is seen that a 24 hour soak had substantially no effect on the stiffness of the polypropylene tubing, but reduced the stiffness of the polyurethane by 62%.

Thus, the invention provides a lubricious anti-infective medical article fabricated from a high melting hydrophilic polymer having up to 10% of a chlorhexidine salt bulk distributed throughout the polymer and a coating of a chlorhexidine salt and a silicone lubricant on the surface. A preferred method to prepare the article includes blending of the polymer and the salt by twin screw compounding, extruding at high temperature and dipping the extruded article in a solvent solution of chlorhexidine and silicone.

What is claimed is:

1. A method for preparing a medical article comprising:
   (a) preparing a blend of a first increment of chlorhexidine and pellets of a substantially hydrophilic polymer selected form the group consisting of polyurethane, polyurethaneurea and siloxane-urethane block copolymer;
   (b) heating said blend to a sufficient temperature and for a sufficient time to form a homogeneous melt of said polymer having said first increment of chlorhexidine uniformly distributed therein;
   (c) extruding said melt through a die to form a medical article having said first increment of chlorhexidine bulk distributed throughout said polymer; and
   (d) applying a coating of silicone lubricant and a second increment of chlorhexidine to the surface of said article having bulk distributed chlorhexidine.

2. The method in accordance with claim 1 wherein said first and second increments of chlorhexidine are selected from the group consisting of chlorhexidine base and about 1 to 10% by weight of a salt thereof.

3. An article produced in accordance with the method of claim 1.

4. The method in accordance with claim 1 wherein said polymer absorbs at least 0.6% of water.

5. The method in accordance with claim 1 wherein said applying step is performed by dipping said article having bulk distributed chlorhexidine into a solution of said silicone and said second increment of chlorhexidine in a solvent.

6. The method in accordance with claim 5 wherein said solvent is selected from the group consisting of ethanol, isopropanol, hexane, dichloro-difluoromethane and mixtures thereof.

7. The method in accordance with claim 1 wherein said melt is formed by twin screw compounding.

8. The method in accordance with claim 1 further comprising wetting said pellets with a polyol prior to said preparing.

9. A method for rendering a medical article fabricated from a polymer selected form the group consisting of polyurethane, polyurethaneurea and siloxane-urethane block copolymer both lubricious and anti-infective comprising applying to a surface of said article a coating comprising a silicone lubricant and an anti-infective agent.

10. A method for preparing a medical article comprising:
   (a) preparing a blend of pellets of a substantially hydrophilic polymer selected from the group consisting of polyurethane, polyurethaneurea and siloxane-urethane block copolymer and about 1 to 10% by weight of a first increment of a salt of chlorhexidine;
   (b) forming a homogeneous melt by twin screw compounding said blend at a temperature of at least 160° C.;
   (c) extruding said melt through a die to form a medical article having said chlorhexidine salt bulk distributed throughout said polymer; and
   (d) dipping said medical article having said first increment of chlorhexidine bulk distributed therein into a solution of a silicone lubricant and a second increment of a chlorhexidine salt to form a coating on said medical article.

11. A medical article comprising a substantially hydrophilic polymer selected from the group consisting of polyurethane, polyurethaneurea and siloxane-urethane block copolymer and a coating thereon, said polymer having a first increment of chlorhexidine bulk distributed throughout and said coating comprising a second increment of chlorhexidine and a silicone lubricant.

12. The article of claim 11 wherein said first and second increments of chlorhexidine are selected from the group consisting of chlorhexidine base and about 1 to 10% by weight of a chlorhexidine salt.

13. An article produced in accordance with the method of claim 9.

14. The article of claim 11 wherein said polymer absorbs at least 0.6% by weight of water.

15. A medical article comprising a substantially hydrophilic polymer selected from the group consisting of polyurethanes, polyurethaneurea and siloxane-urethane block copolymer and a coating of an anti-infective agent and a silicone lubricant.

16. A medical article comprising a polyurethane having a coating thereon, said polyurethane having about 0.1 to 10% by weight of a salt of chlorhexidine bulk distributed throughout, said coating comprising a chlorhexidine salt and a silicone lubricant.

17. The article of claim 16 which is a catheter.

18. The article of claim 16 which is a drainage bag.

19. An article produced in accordance with the method of claim 10.

* * * * *